United States Patent
Herrmann et al.

(10) Patent No.: US 9,377,417 B2
(45) Date of Patent: Jun. 28, 2016

(54) METHOD AND DEVICE FOR MEASURING A MOISTURE VALUE OF DIELECTRIC MATERIALS

(75) Inventors: Rainer Herrmann, Hamburg (DE); Udo Schlemm, Hamburg (DE); Hendrik Richter, Hamburg (DE)

(73) Assignee: TEWS ELECTRONIK DIPL. ING. MANFRED TEWS, Hamburg (DE)

( * ) Notice: Subject to any disclaimer, the term of this patent is extended or adjusted under 35 U.S.C. 154(b) by 1886 days.

(21) Appl. No.: 12/673,701

(22) PCT Filed: Jul. 25, 2008

(86) PCT No.: PCT/EP2008/006102
§ 371 (c)(1),
(2), (4) Date: Dec. 7, 2010

(87) PCT Pub. No.: WO2009/030314
PCT Pub. Date: Mar. 12, 2009

(65) Prior Publication Data
US 2011/0093212 A1     Apr. 21, 2011

(51) Int. Cl.
*G01N 22/04* (2006.01)

(52) U.S. Cl.
CPC .................................. *G01N 22/04* (2013.01)

(58) Field of Classification Search
USPC .......................................................... 702/23
See application file for complete search history.

(56) References Cited

U.S. PATENT DOCUMENTS

| | | | |
|---|---|---|---|
| 4,257,001 A | 3/1981 | Partain et al. | |
| 5,397,993 A | 3/1995 | Tews et al. | |
| 5,666,061 A * | 9/1997 | Assenheim | 324/636 |
| 6,476,619 B1 * | 11/2002 | Moshe | G01N 22/00 324/634 |
| 2005/0150278 A1 * | 7/2005 | Troxler et al. | 73/78 |

FOREIGN PATENT DOCUMENTS

| | | |
|---|---|---|
| DE | 2942971 | 5/1981 |
| DE | 32 41 544 A1 | 10/1984 |
| DE | 37 39 538 A1 | 1/1989 |
| DE | 40 04 119 A1 | 8/1991 |
| DE | 196 45 923 A1 | 5/1998 |
| EP | 0 287 725 A1 | 4/1987 |
| EP | 0665426 | 8/1995 |
| EP | 0 970 369 B1 | 2/1998 |
| EP | 1 703 275 A1 | 2/2006 |
| EP | 1669755 | 6/2006 |

OTHER PUBLICATIONS

"Fast Moisture Profile Maping of a Wet Paper Web With a Dual-Mode Resonator Array" by M. Fischer et al, pp. 607-612.
"Density Independent Moisture Metering in Fibrous Materials Using a Double-Cutoff Gunn Oscillator" by Wolfgang Hoppe, et al, pp. 1449-1452, Copyright 1980 IEEE.
"Electromagnetic Aquametry" by Klaus Kupfer, pp.
"Microwave amd RF Resonator-Based Aquametry" by Alexander S. Sovlukov, Institute of Control Sciences, Moscow, Russia, pp. 169-191.

* cited by examiner

*Primary Examiner* — Mohamed Charioui
(74) *Attorney, Agent, or Firm* — Vidas Arrett & Steinkraus

(57) ABSTRACT

Method for measuring a moisture value F of dielectric materials using at least one microwave resonator, one shift A of the resonant frequency being respectively evaluated for at least two resonance modes with resonant frequencies which are different from one another and a density-independent moisture value being calculated from the measured shifts in the resonant frequency.

26 Claims, 8 Drawing Sheets

METHOD AND DEVICE FOR MEASURING A MOISTURE VALUE OF DIELECTRIC MATERIALS

CROSS-REFERENCE TO RELATED APPLICATIONS

Not applicable.

STATEMENT REGARDING FEDERALLY SPONSORED RESEARCH

Not applicable.

BACKGROUND OF THE INVENTION

The present invention relates to a device and a method for measuring a moisture value of dielectric materials using at least one microwave resonator. The present invention is also suitable, in particular, for granulation, agglomeration, instantisation, coating and drying processes in a fluidised bed or a moving bulk material.

Generally, the use of microwave technology is known for determining mass and/or moisture. It is disclosed in DE 40 04 119 C2 how the effect of variations in density/mass on a moisture signal is prevented when measuring using microwave resonance. To this end, the alteration in the attenuation of the signal, as is indicated, for example, by the alteration in the resonance width or the resonance amplitude, is normalised to the shift in the resonant frequency. Thus the attenuation signal is normalised to a density state which always produces a resonant frequency shift which is proportional to the density. This two-parametric approach, in which in addition to a shift in the resonant frequency the occurring attenuation is also measured, permits a precise measurement of the moisture independently of the density. In particular, when used in fluidised bed dryers, the two-parametric measuring method makes it possible to distinguish accurately between the different effects on the measuring results. In particular, the effects of the variable degrees of granulation is clearly distinguished from the effects of granulation.

EP 0 970 369 discloses a moisture measurement in the high frequency range on a fluidised bed or a moving bulk material with the attenuation of a resonance mode for determining the moisture. The particle size distribution is thus not directly measured in this case, but it is assumed that the total moisture of the product is a direct measurement of the particle size distribution and thus when the moisture is known, the particle size distribution is also known. As the measured attenuation of the microwave signal, on the one hand, always depends on the quantity of material in the measuring field and, on the other hand, depends on the moisture content thereof, by measuring only the attenuation, the effect of a variation in mass and/or density of the sample material on the moisture signal is not able to be compensated. The method, therefore, may only be used for fluidised bed processes and with moving bulk material, in which such a compensation of the density is not required.

An optical measuring head for the on-line examination of the moisture and/or the particle size of agglomerated particles in granulators or dryers is disclosed in DE 196 45 923 A1.

A device for the continuous measurement of moisture in fluidised beds is disclosed in DE 37 39 538 A1. In this connection, a capacitive measurement takes place in two concentric cylinders, the cylinder axes thereof being arranged approximately parallel to the flow of solids. The moisture content is determined via an alteration to the capacity. As, during the capacitive measuring method, the measuring signals depend on the content of mineral material in the sample material, a distinction between the moisture and density (and/or mass/particle size) is not possible in this method.

A method for monitoring and/or controlling during drying, granulation, instantisation, dragee-making and film-coating processes is disclosed in DE 32 41 544 A1. In this case, the moisture of the exhaust air as well as the moisture of the inlet air is measured and the resulting moisture difference is used for controlling the operating process.

The object of the invention is to provide a method and a device for measuring a moisture value which delivers very accurate results by simple means and, in particular when used for moving bulk material or in fluidised beds, may compensate for variations in the mass and/or density of the sample material.

BRIEF SUMMARY OF THE INVENTION

The method according to the invention serves for measuring a moisture value of dielectric materials using at least one microwave resonator. In the method, one respective shift in the resonant frequency is evaluated for at least two resonance modes with resonant frequencies which are different from one another and a density-independent moisture value is calculated from the measured shifts in the resonant frequencies. The particular advantage of this method is that, when determining the moisture value, reference no longer has to be made to an attenuation value as a measurement of the moisture. Instead, from at least two shifts in the resonant frequencies occurring at different resonant frequencies, a density-independent moisture value is calculated with a high degree of reliability. The shift in the resonant frequency results from the difference between the resonant frequency which is present on the empty resonator and the resonant frequency which is present on the filled resonator. In the method according to the invention, the density-independent moisture value is determined, for example, via a moisture calibration curve which provides the moisture value depending on at least two resonant frequency shifts.

In the method according to the invention, the resonant frequencies preferably have a minimum spacing. This minimum spacing is expediently 0.5 GHz or more. Particularly preferably, a minimum spacing of 3.0 GHz may be provided. The resonant frequencies used are preferably in a range of 0.1 GHz to 40.0 GHz.

In a preferred development of the method, the density-independent moisture value F is calculated depending on a quotient of at least two shifts in the resonant frequency. The quotient of two resonant frequency shifts is dependent on the product moisture, but independent of the product mass.

For a density-independent moisture value, use is preferably made of an auxiliary variable $\phi$. A general formula for formulating this auxiliary variable is:

$$\varphi = \frac{\sum_{i=1}^{n} c_1^{(i)} A_i + c_1^{(n+1)}}{\sum_{j=1}^{n} c_2^{(j)} A_j + c_2^{(n+1)}} + c_0$$

the coefficients $c_0$ and $c^{(i)}_1$ as well as $c^{(i)}_2$ where $i=1, \ldots, n+1$ being real numbers.

In the aforementioned general expression it has been assumed that n resonant frequency shifts are considered, which are respectively denoted by $A_j$. In the event that n=2, for linear independent coefficients ($c_1^{(1)}, \ldots, c^{(n+1)}_1$) and ($c_2^{(1)}, \ldots, c^{(n+1)}_2$) for example the following auxiliary variable $\phi$ results:

$$\varphi = \frac{c_1^{(1)}A_1 + c_1^{(2)}A_2 + c_1^{(3)}}{c_2^{(1)}A_1 + c_2^{(2)}A_2 + c_2^{(3)}} + c_0$$

and as a specific case where $c_1^{(2)}=c_1^{(3)}=c_2^{(1)}=c_2^{(3)}=0$:

$$\varphi = \frac{c_1^{(1)}A_1}{c_2^{(2)}A_2} + c_0$$

$c_1^{(1)}, c_2^{(2)}$ and $c_0$ being real numbers, which are adjusted in the conventional manner in a calibration process.

Preferably, the resonant frequency shifts are measured for widely-spaced resonant frequencies. In this case, it has been shown particularly preferably that a lower resonant frequency shift at a frequency of less than two GHz, particularly preferably less than one GHz, is well suited for the evaluation and, in particular, for calculating the auxiliary variable. Also, preferably, an upper resonant frequency shift above 7 GHz, particularly preferably above 10 GHz is taken as a basis. If the auxiliary variable $\phi$ is detected as the quotient of the upper and lower resonant frequency shifts, moisture measurement values may be obtained which are not only density-independent and/or mass-independent, but the measurement results are also substantially independent of the strength of the bond of the water in the product.

In a preferred approach, more than two resonant frequency shifts are measured. The measured values for the resonant frequency shift are adjusted to a dispersion curve A (f). The dispersion curve describes, depending on the frequency, the transition from a resonant frequency shift at low frequency to a resonant frequency shift at high frequency. The formula for the dispersion curve is:

$$A(f) = A_1 + \frac{A_2}{1 + (2\pi f \tau)^2}$$

$A_1$, $A_2$ and $\tau$ being real-value constants, which are adjusted according to the measured values. The constants $A_1$ and $A_2$ of the dispersion curve detected in this manner are subsequently evaluated as a resonant frequency shift at a particularly low frequency and as a resonant frequency shift at a high frequency, in such a manner as if they were measured resonant frequency shifts.

During the measurement of a plurality of resonant frequency shifts, in order to be able to use said resonant frequency shifts for determining the dispersion curve, said resonant frequency shifts have to be normalised to a test piece. By this normalising procedure, it is ensured that the particular field distribution of each individual mode has no effect on the measurement. To this end, a normalising constant K is defined for each measured resonant frequency shift, so that all resonant frequency shifts have the same value on the particular reference body. This particular reference body has the feature that it has no dispersion effect whatsoever in the frequency range considered, i.e. delivers the same value for each measured frequency. It may consist, for example, of Teflon or other synthetic materials. For the reference body, the following applies:

$$A(f1)=K_2 \cdot A(f2)=K_3 \cdot A(f3)=\ldots,$$

$A_i$(fi) denoting the resonant frequency shift in the i-th resonance mode with the resonant frequency fi and $K_2$, $K_3$ etc. being the real-value normalising constants. When adjusting the dispersion curve, the normalised resonant frequency shifts $K_i \cdot A$(fi) are then taken into account.

A particularly preferred feature, in particular when used in fluidised bed processes is to take into account the temperature of the dielectric material to be measured when determining a density-independent moisture value F.

Tests have shown that very good results may be achieved when determining the temperature dependency of a density-independent moisture F with the formula:

$$F(\phi,T)=D_1(T)f(\phi)+D_2(T),$$

$D_1$ (T) and $D_2$ (T) being real functions which are dependent on the temperature T and f ($\phi$) being an auxiliary function dependent on the auxiliary variable $\phi$. In an implementation of this correlation by control engineering, for example, a temperature-dependent family of characteristics may be pre-determined which contains the correlation between the measured value $\phi$ and the density-independent moisture F. Preferably, the auxiliary function f is configured as a monotonously increasing function.

In an expedient embodiment, the auxiliary function f ($\phi$) is the identity transformation, so that the value of the density-independent moisture F is calculated as:

$$F(\phi,T)=D_1(T)\phi+D_2(T).$$

It has also been shown that the arctan function is well suited as an auxiliary function with its limited range, with which the density-independent moisture value F results in:

$$F(\phi,T)=D_1(T)\arctan(\phi)+D_2(T)$$

In a preferred development of the method according to the invention, a moisture-independent density value R is calculated depending on at least two resonant frequency shifts. Expediently, the moisture-independent density value R is also determined depending on the temperature.

By using a further auxiliary function L, which is a function of the individual resonant frequency shifts $A_i$, tests have shown that the temperature-dependency of the moisture-independent density R may be calculated as follows:

$$R(T,A_i)=1_1(T)L(A_i)+1_2(T).$$

The coefficients $1_1$ (T) and $1_2$ (T) are thus real functions which are temperature-dependent.

As an alternative to the auxiliary function L, which is a function of the individual resonant frequency shifts, the moisture-independent density value R may be additionally calculated depending on a product of one of the resonant frequency shifts and the auxiliary variable $\phi$ used when determining the moisture value F.

In a preferred development of the method according to the invention, a moisture-independent mass value M is calculated depending on at least two resonant frequency shifts. Expediently, the moisture-independent density value R is also determined depending on the temperature. Depending on the type of sample material, this mass value may provide information about total mass, surface-related mass or mass per unit of length. The temperature dependency is taken into account in this case as when determining the density.

In a preferred development of the method according to the invention, a particle size D may be additionally calculated from the resonant frequency shift. Such a value is relevant, in particular, when a moving bulk material is measured or measuring takes place in a fluidised bed process.

Generally, a bulk material, small discrete solids, strand-shaped, web-shaped or fibre-shaped solids may be provided as dielectric material for the method according to the invention. All dielectric materials may thus be measured in the mobile or in the static state.

The object of the invention is achieved by a device for measuring a moisture value of dielectric materials according to Claim 19.

The device according to the invention has at least one microwave resonator and an evaluation unit which are configured to determine a shift in the resonant frequency for at least two resonance modes. Moreover, the evaluation unit determines a density-independent moisture value from the at least two shifts in the resonant frequency.

The device according to the invention is preferably provided with a temperature sensor which measures the temperature of the dielectric material and takes into account the measured temperature value when determining the density-independent moisture value. Instead of the temperature of the dielectric material, a temperature in the immediate surroundings thereof may also be measured.

In terms of the structural design of the device, a microwave resonator may be provided with two or more resonance modes, in each case with resonant frequencies which are different from one another. Preferably, the microwave resonator provided is operated with two or more resonance modes as in transmission, but operation in a reflection arrangement is also possible. In this case, for example, it is possible to provide a planar microwave resonator which is designed for at least two resonance modes.

Alternatively or additionally, two or more microwave resonators may also be provided, the resonant frequencies thereof being different from one another. In this case, for example, it may be provided that two or more coaxial resonators are in each case provided as microwave resonators with one resonance mode.

Preferably, the two or more microwave resonators are arranged as closely as possible to one another.

The device, when using two or more microwave resonators, may have a microwave unit for producing two or more resonance modes, a changeover unit being provided which is connected to the two or more microwave resonators, and feeds in each case vibrations produced by the microwave unit into one of the microwave resonators.

Alternatively, it is also possible to provide for each of the microwave resonators a microwave unit for producing a resonance mode in the microwave resonator. The two or more microwave resonators may be connected to one another by a common sample tube, so that the dielectric material to be measured is supplied consecutively or simultaneously to the two or more microwave resonators.

Generally, the device according to the invention has resonant frequencies of which at least two resonant frequencies have a difference of 0.5 GHz. Preferably, the frequency spacing between the resonance modes is 3 GHz or more.

BRIEF DESCRIPTION OF THE SEVERAL VIEWS OF THE DRAWINGS

Preferred embodiments are described in more detail hereinafter with reference to the figures, in which.

DETAILED DESCRIPTION OF THE INVENTION

While this invention may be embodied in many different forms, there are described in detail herein a specific preferred embodiment of the invention. This description is an exemplification of the principles of the invention and is not intended to limit the invention to the particular embodiment illustrated The measuring method according to the invention serves to measure moisture in a density and/or mass-independent manner. It may also be used in order to measure the density and/or the mass and/or the particle size of dielectric materials. Both in industrial processes and in laboratory applications, such methods are of great relevance for controlling the process and also for determining the quality. The method according to the invention is able to be used for all dielectric materials, such as for example bulk materials (grain, coffee, powdered products, tobacco, etc.), small discrete solids (tablets, medical capsules, etc.), large strand-shaped or web-shaped solids (wood, paper, cigarette rods) and textiles (fibre strips, yarn or fabric webs, etc.). The measuring method according to the invention may also be used for specific fluids, for example for acetone.

By means of the disclosed measuring method, in each case the moisture of the sample material may be determined, in specific cases also the density or the mass as well as, for example, in granulates also the particle size of the sample material. The mass of the dielectric material to be determined may be a total mass or the mass per surface unit or unit of length.

The method according to the invention may be used anywhere a density and mass-independent moisture signal is provided for on-line process control. It may also be used, therefore, with rapidly moving sample material. In particular when used in fluidised bed processes, the method according to the invention provides the possibility of improving the process quality.

The method according to the invention is a two-parameter measurement without the use of attenuation of a resonance mode. The two measured parameters are determined by using two resonance modes, the resonant frequencies thereof having a sufficiently large spacing from one another. Preferably, the resonant frequencies are at least 0.5 Gigahertz apart. Expediently, three or more Gigahertz may also be provided as the spacing between the resonant frequencies.

Figure 1:
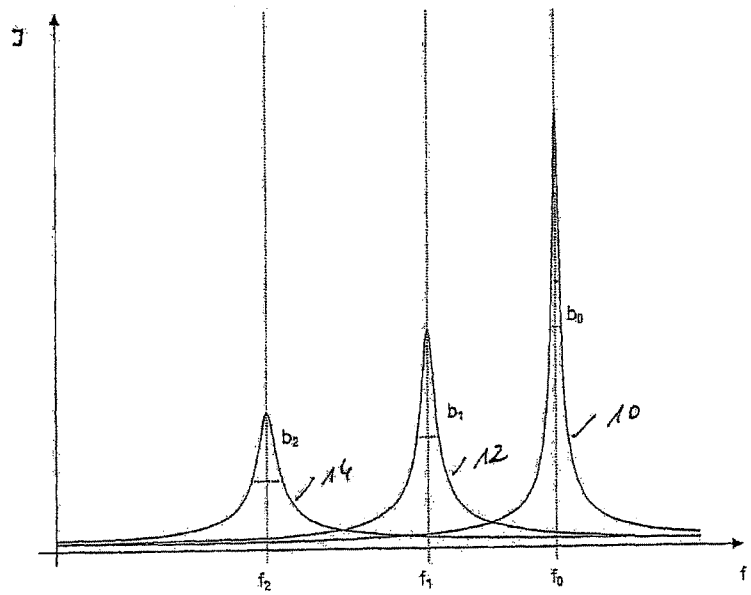
FIG. 1 shows the microwave energy T over the frequency for three resonance modes at different resonant frequencies $f_0, f_1, f_2$.

FIG. 1 shows three resonance curves 10, 12, 14 which in each case are characterised by their resonant frequency $f_0$, $f_1$, $f_2$ and the width of the resonance curve $b_0$, $b_1$ and $b_2$. In the example shown, the amplitude of the resonance curve and/or the microwave energy 10 is markedly greater than the amplitudes of the resonance curves 12 and 14. For the measuring method according to the invention, however, the values of the resonance amplitudes and the widths of the resonance curves $b_0$, $b_1$, $b_2$ are of no relevance when determining the moisture.

The alteration of a resonant frequency of one mode in the resonator, in the field range of which the product is located, relative to the resonant frequency of the same mode of the empty resonator is important for an evaluation of the measuring results.

The difference between the two resonant frequencies is denoted as so-called resonant frequency detuning or resonant frequency shift.

Figure 2:
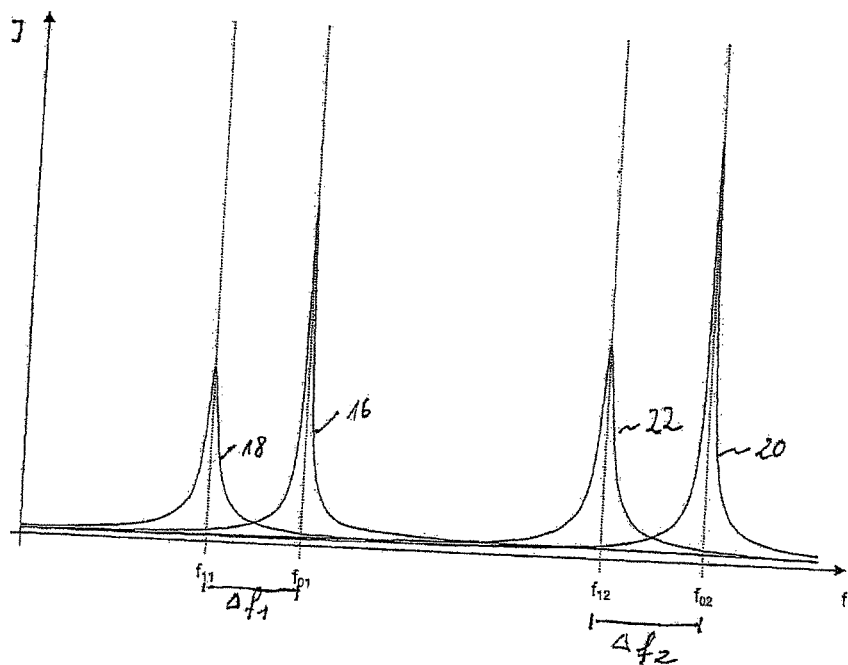
FIG. 2 shows the microwave energy T over the frequency for two resonance modes, in each case in the filled and in the unfilled state of the microwave resonator.

FIG. 2 shows a simple example of two resonant frequency shifts, a first resonance mode having a lower resonant frequency. In FIG. 2 the resonant frequency $f_{01}$ is represented, which shows the frequency response for the first resonant frequency when the resonator is unfilled. The associated resonance curve is denoted by 16. In the filled state of the resonator, the resonant frequency $f_{11}$ results with the resonance curve 18. Also illustrated is the resulting resonant frequency $\Delta f_1$ for the first frequency. The resonant frequency shift in the resonant frequencies passes through the product to be measured. The resonant frequency $f_{02}$ is also shown for the higher frequency. The associated resonance curve is denoted by 20. A shift in the resonant frequency $f_{02}$ passes through the material to be measured up to the value $f_p$. The associated resonant frequency shift is shown as $\Delta f_2$ in FIG. 2.

The measuring values $\Delta f_1$, $\Delta f_2$ are considerably influenced by the mass of the product to be measured which is located in the field range of the microwave resonator.

When using powdered material, the measuring values $\Delta f_1$, $\Delta f_2$ also depend on the granulate size. With planar material having a thin layer thickness, the measuring result is highly dependent on the measured layer thickness.

The measuring values $\Delta f_1$, $\Delta f_2$ for each resonance mode, the measuring field thereof being passed through by the product, are proportional to the mass of the product in the measuring field. This means that when the measuring field is completely filled up, the measuring values are proportional to its density. As the dielectric constant of water is substantially greater than the dielectric constant of dry substances, the measuring values $\Delta f_1$, $\Delta f_2$ also depend considerably on the moisture of the material. The dielectric constant of free water additionally is highly dependent on the frequency in the microwave range. Above a frequency of one Gigahertz, it reduces markedly as the frequency increases and with frequencies of over 30 Gigahertz it approaches a low value determined by the electron distribution of the atom. This means that the dielectric constant of moist sample material is lower at a high frequency than at a lower frequency.

If $\Delta f_1$ is the resonance detuning relative to the empty state of a material to be measured in the first resonance mode at the empty resonant frequency $f_{01}$ and if $\Delta f_2$ is the resonant frequency detuning relative to the empty state of a material to be measured in the second resonance mode with an empty resonant frequency $f_{02}$, then the values $\Delta f_1$, $\Delta f_2$ are respectively proportional to the mass. $\Delta f_1$ and $\Delta f_2$, however, depend in a variable manner on the moisture of the material, when the two resonant frequencies of the modes are spaced sufficiently far apart from one another. It has been shown that a spacing of $|f_{02}-f_{01}| \geq 0.5$ Gigahertz is already a sufficiently large spacing. Clearer measuring results may be achieved if the spacing of the resonant frequency is $|f_{02}-f_{01}| \geq 3.0$ Gigahertz.

Tests have shown that the quotient $\Delta f_2/\Delta f_1$ is independent of the product mass but is a measurement of the product moisture. The quotient is calibrated as an indirectly measured moisture value on a directly measured reference moisture. Hereinafter:

$A1=\Delta f_1$ and $A2=\Delta f_2$.

It may be provided in order to limit the value range of the microwave measured values, to use an auxiliary variable $\phi=\arctan(A2/A1)$.

Measuring results show that when in a coordinate system the reference values A2 are plotted against A1, the measuring points of variable mass but the same moisture are located on a straight line and said measuring points run through the zero point. Measuring points of the same moisture but variable mass are respectively located on straight lines, the slope thereof being moisture-dependent.

In particular, measurements with high moisture and high density have shown that these different straight lines in the A1, A2 coordinate system do not necessarily pass through the zero point. Thus, for example, it may be the case that straight lines for variable mass at constant moisture do not pass through the origin.

In this case, the A1 and the A2 values of the point of intersection may be shifted by constant terms $A_1^{(0)}$ and $A_2^{(0)}$, so that the following expression results as a density-independent auxiliary variable $\phi$:

$$\varphi = \frac{A2 - A_2^{(0)}}{A1 - A_1^{(0)}}$$

The arctan may again be applied to this auxiliary variable $\phi$ for limiting the range.

For increasing the measuring accuracy, not only two resonance modes located sufficiently far apart may be brought into interaction with the sample material, but also three, four or more. In this case, coupling parameters K may be defined for the individual resonance modes. The coupling parameters K are determined for the individual resonance modes using a standard test piece, so that the resonant frequency detailing of the first mode A1 when measuring the standard test piece leads to the same resonant frequency shift as in the other resonance modes, if the same standard test piece is used. If, for example, four resonance modes are considered, the following equation of condition for the coupling parameters K2, K3 and K4 results:

$A(f1)=K2 \cdot A(f2)=K3 \cdot A(f3)=K4 \cdot A(f4)$ (when measuring the standard test piece).

The method according to the invention, which has already been disclosed above for two resonance modes, may be combined directly into four resonance modes, if for example a linear combination of the four resonant frequency shifts is considered as a first value, and in turn a linear combination of the four resonant frequency shifts are set as a second measured value. The only important aspect is that the measured values thus formed contain linear combinations of the resonant frequency shifts, which are independent of one another in linear terms.

For compensating the temperature effect on the density-independent moisture F, the product temperature T is measured by a separate temperature sensor. Tests have shown that a linear effect of the product temperature T on the coefficients on the moisture curve is sufficient. If the following formula is selected for the density-independent moisture:

$$F(\phi,T)=C1(T)\cdot\arctan(\phi)+C2(T),$$

the temperature coefficients C1 and C2 are sufficiently accurately represented, respectively by a linear dependency on the temperature. The following results:

$$C1=C_1^{(1)}\cdot T+C_1^{(2)},$$

$$C2=C_2^{(1)}\cdot T+C_2^{(2)},$$

with the real coefficients $C_1^{(1)}$, $C_2^{(1)}$, $C_2^{(1)}$, $C_2^{(2)}$. If by the above methods a value has been calculated dependent only on the material moisture which, however, is independent of the material density, the material mass—as well as the particle size, by using a value A1, A2 proportional to the mass by using the auxiliary variable $\phi$, which is only moisture-dependent, the mass M in the measuring field and/or the material density R and/or the particle size K may be determined. In this connection, it is important that the auxiliary variable $\phi$ is moisture-dependent and mass-independent. As a result, it is provided by means of $\phi$ to determine a correction of the mass-dependent value A1, A2 and thus to calculate the moisture component.

As already occurs when measuring the moisture, in this case measuring results have shown that a linear approach for evaluating the measured values already delivers very good results. For determining a moisture-independent mass value the formula is selected:

$$M=D2A2+D1A1\cdot\phi+D0,$$

D0, D1, D2 being real numbers.

With this formula it is clear that the mass M is calculated from a mass-dependent component A2, which is corrected by a component $\phi$ which is only moisture-dependent.

In an alternative formula, the mass may also be calculated so that:

$$M=D1A1+D2A2+D0$$

These formulae may also be used for evaluating a density R, if by the design of the measuring process it is ensured that the microwave resonator is completely filled with mass, i.e. the entire measuring field of the resonator is filled with sample material.

These formulae are also relevant for determining a particle size K in bulk materials and in fluidised bed processes.

Even when determining the mass and/or density and/or the particle size, a temperature-dependent correction of the measured value may take place. Also in this case, it is again provided to represent the coefficients D1, D2, with which the resonant frequency shift is incorporated in the measured result, as temperature-dependent:

$$D1=D_1^{(1)}\cdot T+D_1^{(2)},$$

$$D2=D_2^{(1)}\cdot T+D_2^{(2)},$$

Figure 3:
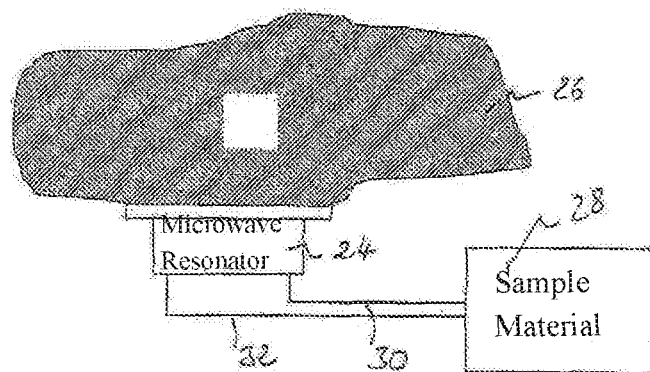
FIG. 3 shows a resonator arrangement for measuring the transmission, 0

FIG. 3 shows in a very schematic view a possible device-related implementation of the invention. FIG. 3 shows a planar microwave resonator 24 operated in transmission, the field thereof penetrating a sample material 26. The dielectric constant of the sample material 26 has the result that the resonance modes of the resonator 24 are altered in a characteristic manner. In the microwave unit 28, microwaves are produced at variable frequency by a microwave generator and returned to the microwave resonator 24 via a first coaxial cable 30. In this case, the microwaves are coupled into the resonator by an antenna. Different resonance modes are formed in the resonator, the field lines thereof reaching as far as the sample material 26. By a further antenna (not shown) in the microwave resonator 24, the microwaves are decoupled from the resonator and supplied via a second coaxial cable 32 to the microwave unit 28. The determination of the resonant frequencies of the filled resonator takes place here. By the comparison with the previously determined resonant frequencies of the empty microwave resonator there is then the possibility of determining the resonant frequency shifts as a result of the sample material 26. A resonant frequency may, for example, be determined via the maximum point in the resonance curve. Alternatively, it is also possible to view the phase shift in the reflected field relative to the transmitted field. In the resonant frequency a zero transition in the phase shift is present from the incoming wave to the outgoing wave.

If a microwave resonator is operated in reflection, an embodiment with a microwave coaxial cable between the evaluation unit and the microwave resonator is sufficient. The microwave energy reflected via this cable is measured. The occurrence of resonance is then identified when a minimum of the reflected energy is present.

Figure 4:
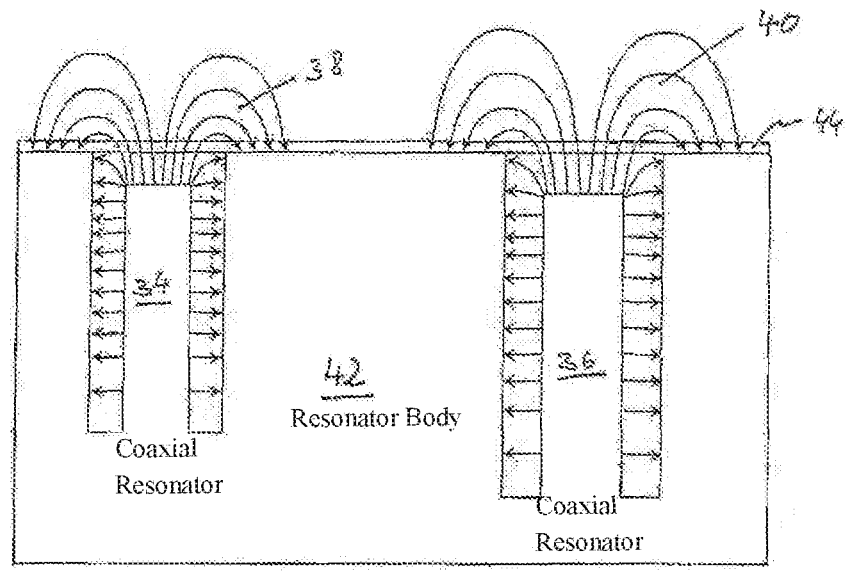
FIG. 4 shows a schematic cross-sectional view of two coaxial resonators, with in each case one resonance mode, which are arranged adjacent to one another and have different resonant frequencies.

FIG. 4 shows the more detailed construction of a microwave resonator. In this case there are two coaxial resonators 34 and 36. Resonator 34 is provided for the higher resonant frequency, whilst resonator 36 has a lower resonant frequency. In each of the resonators 34 and 36, field lines 38, 40 emerge from the resonator body 42. The resonator may be protected by a dielectric cover plate 44. In this resonator is located the sample material to be measured in the region of the emerged field lines 38 and 40.

Figure 5:
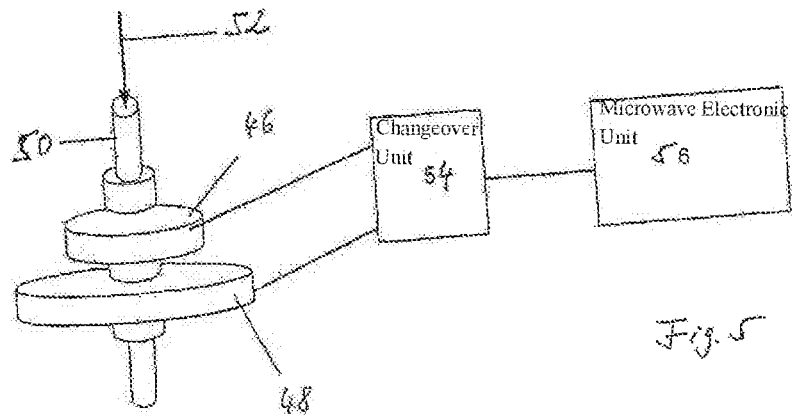
FIG. 5 shows two resonators, with in each case one resonance mode, which are connected via a changeover switch to a microwave electronic unit.
Figure 6:
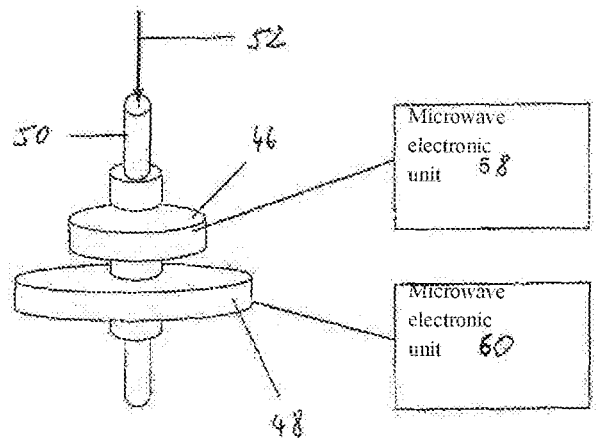
FIG. 6 shows two resonators, with in each case one resonance mode, which are connected to one respective microelectronic unit.

FIGS. 5 and 6 show a further embodiment in which the product is measured by different resonators, the resonant frequencies thereof being spaced widely apart. FIG. 5 shows two superimposed microwave resonators 46, 48 which are connected to one another via a sample tube 50. The schematically indicated material flow 52 is supplied via the sample tube 50 initially to the microwave resonator 46 and emerges therefrom and passes into the microwave resonator 48. It is clearly visible that for accurate measurement the distance between possible non-uniformities present in the sample material has to be markedly greater than the spatial distance between the two resonators 46 and 48.

In the embodiment shown in FIG. 5, a microwave electronic unit 56 is provided which has a microwave generator, a microwave detector and a CPU. Via a microwave changeover unit 54, the signals are forwarded to the microwave resonators 46 or 48. The returning signals of the two microwave resonators also flow over the changeover unit 54 back to the microwave electronic unit for evaluation.

FIG. 6 shows in principle a similar design of microwave resonators as in FIG. 5. However, the microwave changeover unit is dispensed with, and instead two microwave electronic units 58 and 60 are provided which generate the microwaves coupled into the resonators 46 and 48, detect the uncoupled components and evaluate the measured resonance values.

Figure 7:
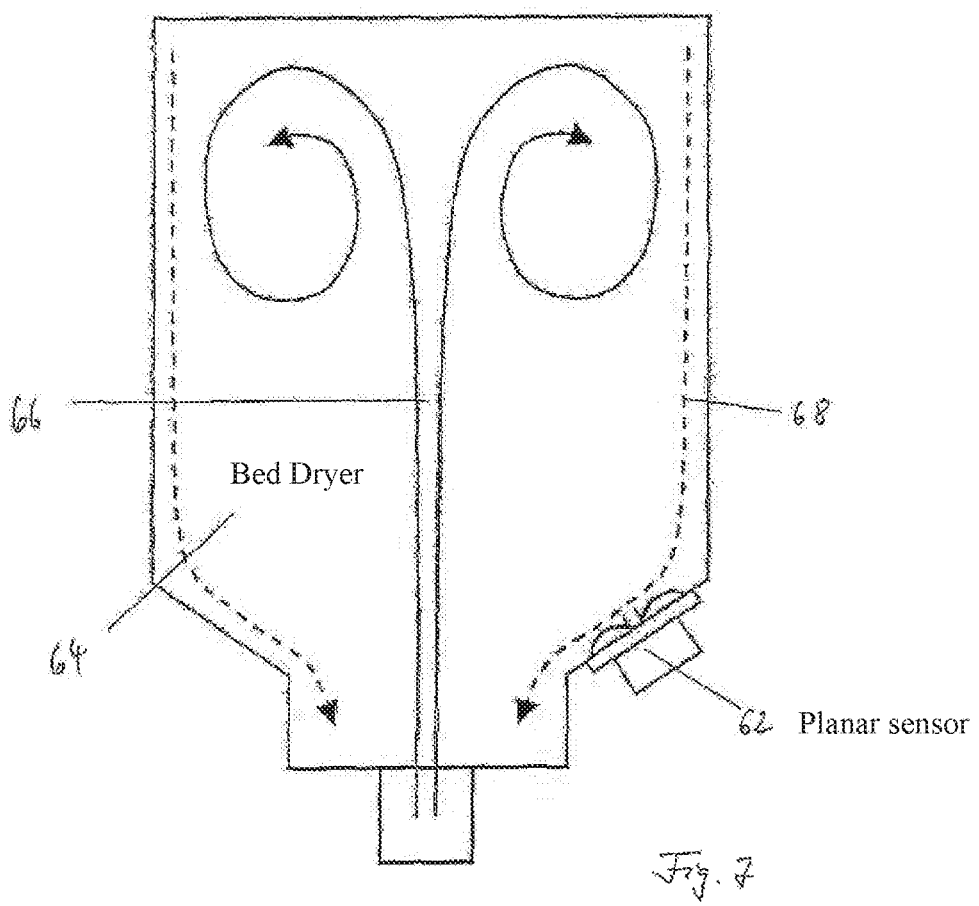
FIG. 7 shows the use of a planar sensor in a fluidised bed dryer.

FIG. 7 shows the application of a planar sensor 62 in a schematically shown fluidised bed dryer 64. In the fluidised bed dryer, shown by way of example, heating air 66 is blown in centrally which leads to a movement of the material 68. In the course of the material movement 68, the material is passed along a conical tapered portion of the fluidised bed dryer 64 past a planar sensor 62, which in at least two resonance modes is able to carry out measurements with the required frequency spacing.

In the example shown in FIG. 7, the microwave resonator 62 is arranged in a shoulder portion of the fluidised bed dryer.

In this manner it is ensured that a uniform material flow passes the microwave resonator 62.

As a result of the moisture and density measurement in the fluidised bed process, it is possible to control said fluidised bed process. It is, for example, possible to control or to regulate the average particle size during the granulation phase. As already shown above, the method with the auxiliary variable φ also permits an on-line measurement of the particle size. The measured particle size is forwarded to a control unit of a dryer, in order to control the process parameter thereof, such as for example the temperature. Moreover, the final point of the drying process may also be established by the density-independent moisture measurement, by the drying process being switched off when reaching a predetermined final moisture level.

Figure 8:
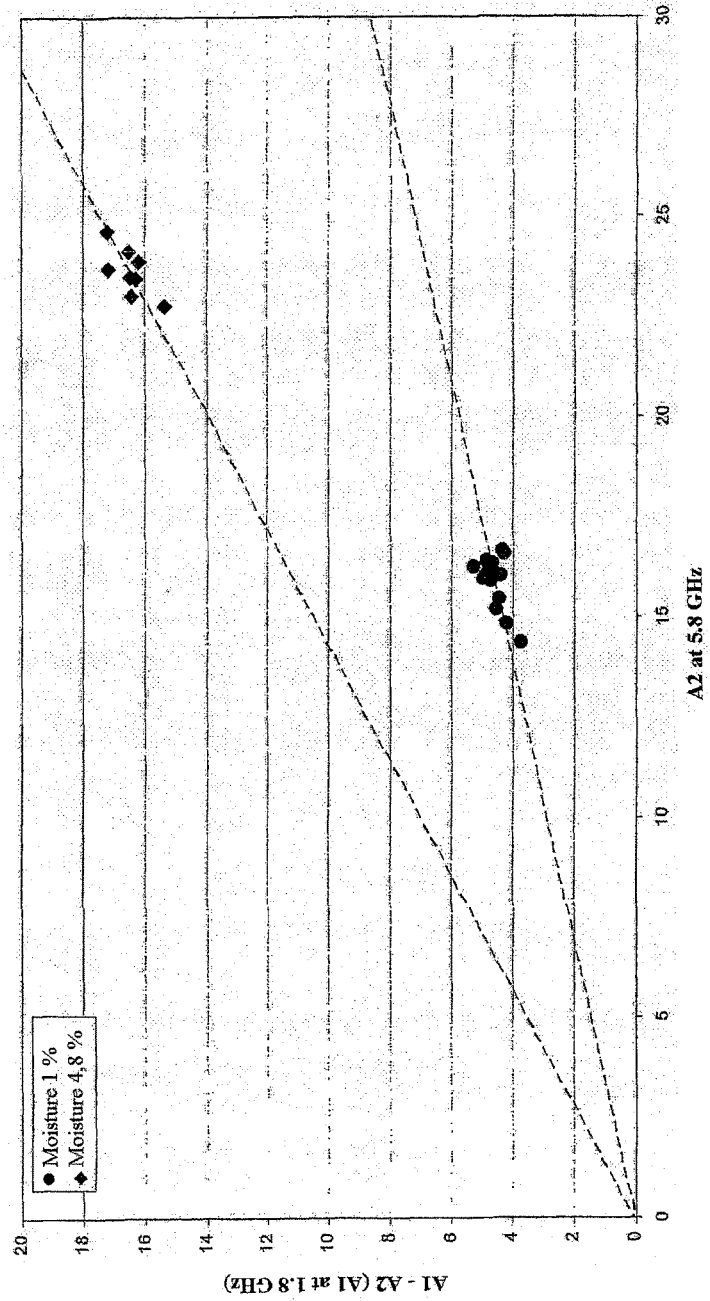
FIG. 8 shows a measuring example for measuring moisture on lactose granulate from a fluidised bed process, resonant frequency shifts in two resonance modes being plotted above one another for different densities and moistures.

FIG. 8 shows by way of example the measurement of moisture on lactose granulate from a fluidised bed process with a planar resonator with a plurality of resonance modes. Measuring points with two different moistures (1% and 4.8%) and different densities are shown. Measurements were carried out in two different resonance modes (1.8 GHz and 5.8 GHz). In this case, the difference of the resonant frequency shifts $A_1-A_2$ is plotted over the resonant frequency shift in the mode at the higher frequency $A_2$. It is shown that the points of the same moisture are located on straight lines and their position on this straight line is determined by the respective material density and/or the material mass in the measuring field. The points with variable moisture are located on straight lines through the coordinate origin, the slope thereof being moisture-dependent. The density-independent moisture value is calculated in this example from the auxiliary variable $\phi=(A_1-A_2)/A_2$.

Figure 9:
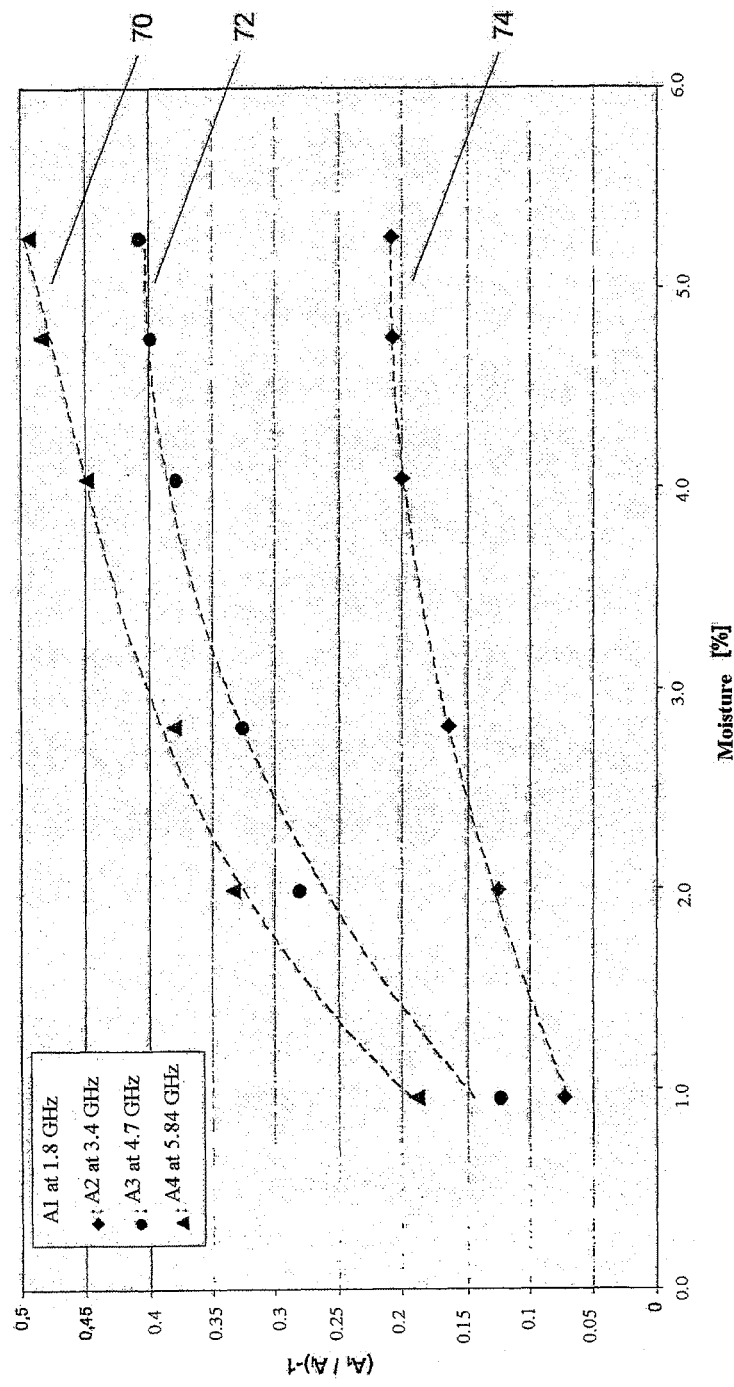
FIG. 9 shows a further measuring example for measuring moisture on lactose granulate from a fluidised bed process using a planar resonator with a plurality of resonance modes.

FIG. 9 shows by way of example the measurement of moisture on lactose granulate from a fluidised bed process with a planar resonator with a plurality of resonator modes. The auxiliary variable φ is shown respectively for the moisture measurement, which is formed from the quotient of two resonant frequency shifts $A_1$ and $A_i$ (i=2, 3, 4) according to the following rule: $\phi=(A_1/A_i)-1$. The different curves 70, 72, 74 show, for different samples, the value of the auxiliary variables $(A_1/A_i-1)$ for resonance modes at 3.4 GHz $(A_2)$, 4.7 GHz $(A_3)$ and 5.84 GHz $(A_4)$. The dependence of the measured values on the moisture is clearly identifiable, the measuring effect being greater the further the measured resonance modes are spaced apart.

Figure 10:
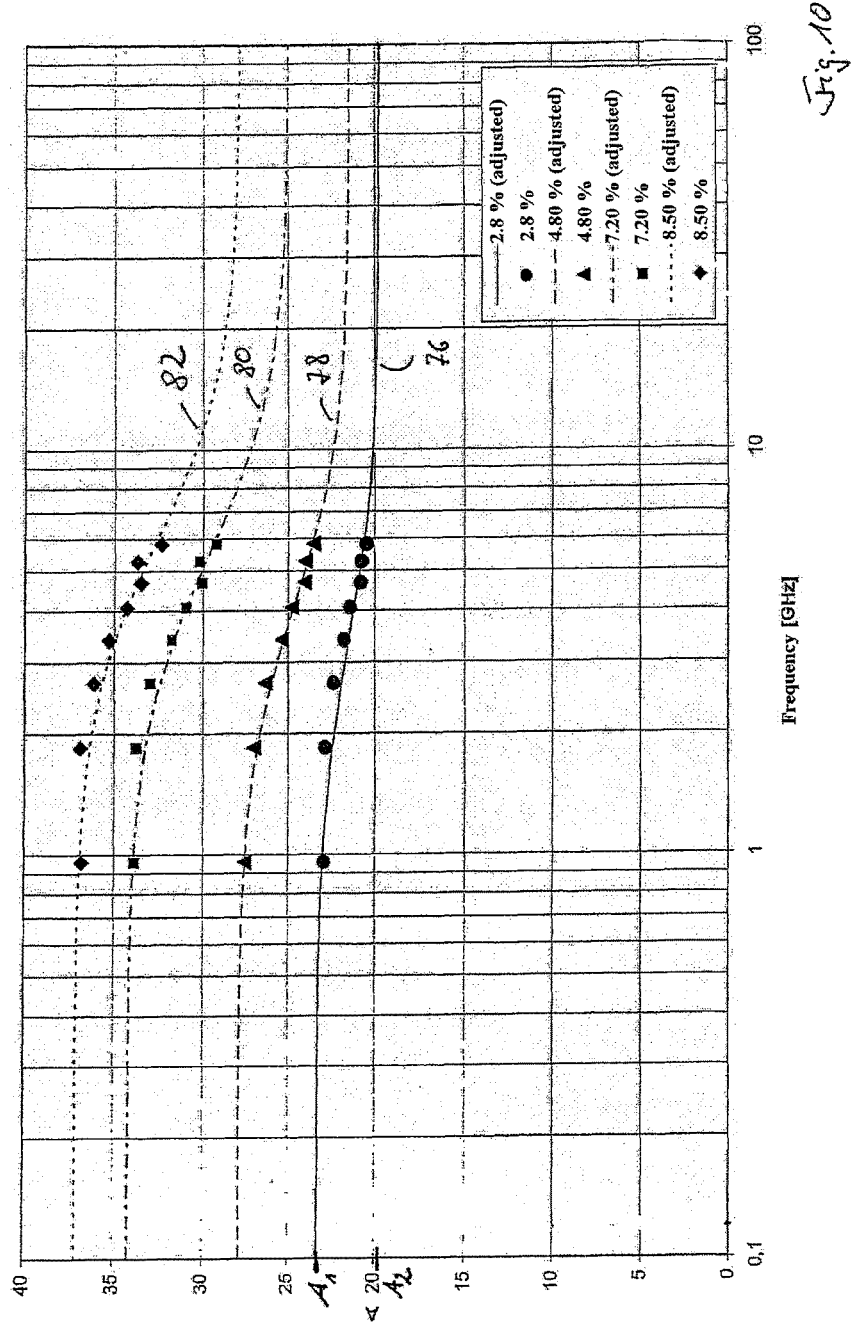
FIG. 10 shows a set of dispersion curves for the dependency of the resonant frequency shift on the logarithmically plotted frequency.

FIG. 10 shows a set of dispersion curves 76, 78, 80 and 82. The curves show the resonant frequency shift A over the logarithmically plotted frequency f. The illustrated measuring points correspond to the measurement of a test piece at different moisture values. At a moisture of 2.8%, the assumed measured values (filled circuit) are very compatible with the curve 76. Also the measured values at 4.8% moisture, 7.2% moisture and 8.5% moisture, are very close to the respectively adjusted curves 78, 80 and 82. From the curves which have a general path $$A(f) = A_1 + \frac{A_2}{1+(2\pi f \tau)^2}$$

$A_1$ and $A_2$ describing the resonant frequency shifts at low and very high frequency and τ being a measurement of the strength of the water bond. The values $A_1$ and $A_2$ determined from the measurement curve are illustrated for the curve 76 by way of example in FIG. 10. The values $A_1$ and $A_2$ provide information about the resonant frequency shift, respectively at a very low frequency and/or at a very high frequency. The values $A_1$ and $A_2$ may be evaluated by the method according to the invention as if they were measured values.

Figure 11:
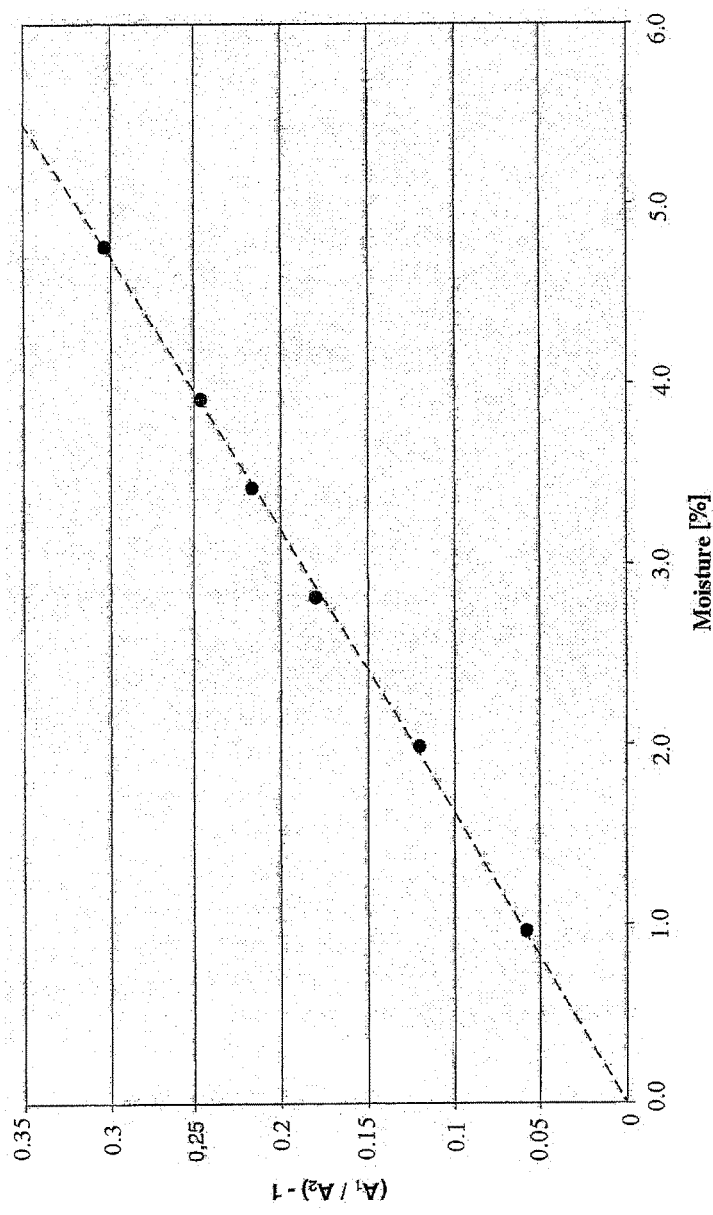
FIG. 11 shows the moisture calibration curve independent of the density and bond obtained from FIG. 10.

FIG. 11 shows the values obtained from the A1 and A2 values of FIG. 10

$$\varphi = \frac{A_1}{A_2} - 1$$

as a function of the moisture. This moisture calibration curve is not only mass-independent and density-independent but also independent of the strength of the bond of the water in the product. This also means a marked reduction of the effect of temperature on the calibration.

The particular advantages of the invention relative to the previously known measured samples result from the fact that an attenuation measurement is no longer necessary, but merely a resonant frequency and/or the shift thereof has to be detected. As the frequency at maximum resonance amplitude may be substantially more easily measured than, for example, the resonance width at half amplitude, the measurement may be carried out considerably more rapidly than the previous measuring methods. For the measurement of the resonance width, for example in terms of frequency, the entire resonance curve has to be passed through and measured. This leads to problems, for example, with mobile materials, as the sample material is not allowed to be displaced when passing through the resonance curve. In contrast thereto, in the new measuring method only the region of maximum resonance needs to be examined, so that movements of the product during the measuring process do not cause interference. Even with fluidised bed processes and with moving bulk materials, therefore, a rapidly moved product may also be easily measured.

A further advantage of the method according to the invention results from a comparison with the previous attenuation and width measurement of the resonance curve: with greater attenuation values, non-linearities of the microwave diodes, which may falsify the measured result, are important. In contrast thereto, in the present measuring method, non-linearities of the microwave diodes are not important.

A further particular advantage results from the fact that the variation of the frequency may move in a narrow range around the maximum level of the current resonance. In contrast to an attenuation measurement, it is no longer necessary to pass through the entire resonance curve. As a result, a high-speed measurement at $10^4$ to $10^5$ measured values per second is possible.

Also, the microwave resonator itself may be designed considerably more simply for the method according to the invention than for an attenuation measurement. Thus, for example, complicated and expensive microwave isolators for preventing backscatter into the electronics may be dispensed with.

In contrast to conventional measuring methods, which also operate according to microwave resonance methods, in the invention the requirement for complete absence of emission from the microwave resonators may be dispensed with. Emission in which the resonator loses part of its vibrational energy in the form of emitted microwaves during microwave measurement, generally always has the effect of increasing the width of the resonance curve. A measurement of the attenuation or width thus absolutely requires maintaining the requirement for complete absence of emission from the resonator. Otherwise, the measured losses are attributed to the moisture of the product, i.e. they lead to substantial measuring errors. According to the invention, attenuation measurement is dispensed with, so that within certain tolerances emission of microwaves is also permitted. As a result, microwave modes with a relatively large stray field and a specific level of emission may also be used, provided the emission does not influence the resonant frequency too greatly. A particular advantage of the method according to the invention when using planar sensors is that the penetration depth is increased so that, for example, a contact measurement may be dispensed with.

The resonant frequency shifts may be also detected easily on-line in fluidised bed processes, in order to generate thereby reliable moisture values for a control of the granulation process and a subsequent drying process.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A method for measuring a density-independent moisture value F of dielectric materials, comprising the steps of:
providing at least one microwave resonator;
evaluating a shift A in a resonant frequency of an empty resonator, relative to a resonator in the field range of which the dielectric material is located, wherein the shift A in the resonant frequency is the difference between the resonant frequency of the empty resonator and the resonant frequency of the resonator with the dielectric material located in the field range of the resonator, the shift A being evaluated for at least two resonance modes with resonant frequencies which are different from one another;
calculating the density-independent moisture value F from at least two evaluated shifts A, the density-independent moisture value F being calculated depending on at least one quotient of the at least two evaluated shifts A,
wherein the at least two resonance modes respectively having a resonant frequency which have a spacing from one another of at least 0.5 GHz, and
further wherein that in a granulation, instantisation, coating or drying process, the measured moisture value is forwarded to a process control which controls and/or regulates the process depending on the applied moisture value.

2. The method according to claim 1, characterised in that three or more measuring points for the resonant frequency shift are determined from a dispersion curve A (f) of the following form $$A(f) = A_1 + \frac{A_2}{1 + (2\pi f \tau)^2}$$

$A_1$, $A_2$ and $\tau$ being real-value constants, of which $A_1$ and $A_2$ are established according to the measured values.

3. The method according to claim 2, characterised in that the values $A_1$ and $A_2$ from the dispersion curve are set and evaluated as resonant frequency shifts at a low frequency and at a high frequency.

4. The method according to claim 1, characterised in that the density-independent moisture value F is calculated depending on the temperature T of the measured dielectric material.

5. The method according to claim 1, characterised in that additionally a moisture-independent density value R is calculated depending on the at least two shifts.

6. The method according to claim 5, characterised in that the moisture-independent density value R is determined depending on the temperature.

7. The method according to claim 6, characterised in that the moisture-independent density value R is additionally calculated depending on a product of a resonant frequency shift and an auxiliary variable $\phi$.

8. The method according to claim 1, characterised in that additionally a moisture-independent mass value M is calculated depending on the at least two shifts.

9. The method according to claim 8, characterised in that the moisture-independent mass value M is determined depending on the temperature.

10. The method according to claim 9, characterised in that the moisture-independent mass value M is additionally calculated depending on the product of a resonant frequency shift and an auxiliary variable $\phi$.

11. The method according to claim 1, characterised in that a particle size D is additionally calculated from the resonant frequency shifts.

12. The method according to claim 1, characterised in that a bulk material, small discrete solids, strand-shaped, web-shaped or fiber-shaped solids are provided as dielectric material.

13. The method according to claim 1, characterised in that the density-independent moisture value is determined independently of attenuation occurring in each of the resonance modes.

14. The method according to claim 1, characterised in that the density is determined independently of attenuation occurring in each of the resonance modes.

15. The method according to claim 1, characterised in that the process control using the measured moisture values determines a process end or an end of a process stage.

16. A device for measuring a moisture value of dielectric materials, comprising:
at least one microwave resonator and at least one evaluation unit, which are configured to determine at least two shift in the resonant frequency of an empty resonator relative to the resonator in the field range of which the dielectric material is located, for at least two resonance modes and in order to determine a density-independent moisture value from the at least two shifts in the resonant frequency, a microwave resonator being provided with two or more resonance modes with different resonant frequencies, respectively having a resonant frequency which have a spacing from one another of at least 0.5 GHz, and further wherein that in a granulation, instantisation, coating or drying process, the measured moisture value is forwarded to a process control which controls and/or regulates the process depending on the applied moisture value.

17. The device according to claim 16, characterised in that at least one temperature sensor is provided which measures the temperature T of the dielectric material and the evaluation unit determines the density-independent moisture value F depending on the temperature T.

18. The device according to claim 16, characterised in that, as microwave resonators, two coaxial resonators are each provided with a resonance mode.

19. The device according to claim 16, characterised in that a planar microwave resonator is provided with at least two resonance modes.

20. The device according to claim 16, characterised in that two or more microwave resonators are provided, the resonant frequencies thereof being different from one another.

21. A method for measuring a density-independent moisture value F of dielectric materials, comprising the steps of:
providing at least one microwave resonator;
evaluating a shift A in a resonant frequency of an empty resonator, relative to a resonator in the field range of which the dielectric material is located, wherein the shift A in the resonant frequency is the difference between the resonant frequency of the empty resonator and the resonant frequency of the resonator with the dielectric material located in the field range of the resonator, the shift A being evaluated for at least two resonance modes with resonant frequencies which are different from one another;
calculating the density-independent moisture value F from at least two evaluated shifts A, the density-independent moisture value F being calculated depending on at least one quotient of the at least two evaluated shifts A, wherein the at least two resonance modes respectively having a resonant frequency which have a spacing from one another of at least 0.5 GHz, and further wherein that in a granulation, instantisation, coating or drying process, the measured value for mass, density and/or particle size is forwarded to a process control, which controls and/or regulates the process depending on the applied values for mass, density and/or particle size.

22. A device for measuring a moisture value of dielectric materials, comprising:
at least one microwave resonator and at least one evaluation unit, which are configured to determine at least two shift in the resonant frequency of an empty resonator relative to the resonator in the field range of which the dielectric material is located, for at least two resonance modes and in order to determine a density-independent moisture value from the at least two shifts in the resonant frequency, a microwave resonator being provided with two or more resonance modes with different resonant frequencies, respectively having a resonant frequency which have a spacing from one another of at least 0.5 GHz,
wherein that in a granulation, instantisation, coating or drying process, the measured value for mass, density and/or particle size is forwarded to a process control, which controls and/or regulates the process depending on the applied values for mass, density and/or particle size.

23. The device according to claim 22, characterised in that at least one temperature sensor is provided which measures the temperature T of the dielectric material and the evaluation unit determines the density-independent moisture value F depending on the temperature T.

24. The device according to claim 22, characterised in that, as microwave resonators, two coaxial resonators are each provided with a resonance mode.

25. The device according to claim 22, characterised in that a planar microwave resonator is provided with at least two resonance modes.

26. The device according to claim 22, characterised in that two or more microwave resonators are provided, the resonant frequencies thereof being different from one another.

* * * * *